(12) United States Patent
Suzuki et al.

(10) Patent No.: US 7,902,467 B2
(45) Date of Patent: Mar. 8, 2011

(54) BIOMETRIC APPARATUS WITH AUTOMATIC ZERO-POINT RESET FUNCTION

(75) Inventors: Shun Suzuki, Tokyo (JP); Masaki Yoshizawa, Tokyo (JP); Kazuyasu Koyama, Tokyo (JP); Kosei Fukada, Tokyo (JP)

(73) Assignee: Tanita Corporation, Tokyo (JP)

( * ) Notice: Subject to any disclaimer, the term of this patent is extended or adjusted under 35 U.S.C. 154(b) by 233 days.

(21) Appl. No.: 12/155,957

(22) Filed: Jun. 12, 2008

(65) Prior Publication Data

US 2008/0314648 A1 Dec. 25, 2008

(30) Foreign Application Priority Data

Jun. 15, 2007 (JP) ................................. 2007-159509

(51) Int. Cl.
*G01G 23/01* (2006.01)
(52) U.S. Cl. .............................. 177/50; 702/101; 73/1.13
(58) Field of Classification Search .................. 702/101, 702/102; 177/50, 185; 73/1.13; 600/372, 600/547
See application file for complete search history.

(56) References Cited

U.S. PATENT DOCUMENTS

| | | | | |
|---|---|---|---|---|
| 4,082,153 A * | 4/1978 | Provi | ............................. | 177/177 |
| 4,379,495 A * | 4/1983 | Cocks et al. | ...................... | 177/1 |
| 4,494,620 A * | 1/1985 | Knothe et al. | ............. | 177/25.13 |
| 4,553,619 A * | 11/1985 | Fujinaga | ........................ | 177/185 |
| 4,660,160 A * | 4/1987 | Tajima et al. | ................. | 702/173 |
| 4,660,662 A * | 4/1987 | Katz | ................................ | 177/50 |
| 4,715,457 A * | 12/1987 | Amacher et al. | ................... | 177/1 |
| 4,782,904 A * | 11/1988 | Brock | ............................ | 177/185 |
| 4,858,161 A * | 8/1989 | Baumann | ....................... | 702/101 |
| 5,056,050 A * | 10/1991 | Fuchs et al. | .................... | 702/101 |
| 5,074,368 A * | 12/1991 | Bullivant | ........................ | 177/50 |
| 5,125,465 A * | 6/1992 | Schneider | ....................... | 177/50 |
| 5,143,164 A * | 9/1992 | Nahar | ............................. | 177/50 |
| 5,646,376 A * | 7/1997 | Kroll et al. | .................... | 177/211 |
| 6,080,938 A * | 6/2000 | Lutz | ........................... | 177/25.15 |
| 6,137,065 A * | 10/2000 | Zefira | ........................ | 177/25.13 |
| 6,215,078 B1 * | 4/2001 | Torres et al. | ............... | 177/25.15 |
| 6,236,001 B1 * | 5/2001 | Shymko | ........................ | 177/149 |
| 6,794,586 B1 * | 9/2004 | Mason | ........................ | 177/25.15 |
| 6,838,624 B2 * | 1/2005 | Chan | ............................... | 177/50 |
| 6,995,323 B2 * | 2/2006 | Kunzi et al. | ................ | 177/25.13 |
| 7,497,137 B2 * | 3/2009 | Tellenbach et al. | .......... | 73/865.9 |
| 2009/0088661 A1 * | 4/2009 | Suzuki et al. | ................ | 600/547 |

FOREIGN PATENT DOCUMENTS

JP 62-126318 6/1987

* cited by examiner

*Primary Examiner* — Randy W Gibson
(74) *Attorney, Agent, or Firm* — McDermott Will & Emery LLP

(57) ABSTRACT

A biometric apparatus includes a weight measuring unit having a predetermined zero-point for measuring a load applied to a platform provided on a body of the biometric apparatus and outputting a load signal which indicates the load; a detecting unit for detecting the state of installation of the biometric apparatus and outputting a detection signal indicating the same; and a control unit connected to the weight measuring unit and the detecting unit for determining whether or not the state of installation is suitable for the zero-point reset of the weight measuring unit on the basis of the detection signal and whether or not the load signal is stabilized, and the zero-point reset is carried out when the control unit determines that the state of installation is suitable for carrying out the zero-point reset for the weight measuring unit and the load signal from the weight measuring unit is stable.

6 Claims, 6 Drawing Sheets

BIOMETRIC APPARATUS WITH AUTOMATIC ZERO-POINT RESET FUNCTION

BACKGROUND OF THE INVENTION

1. Field of the Invention

The present invention relates to a biometric apparatus for measuring biometric data and, more specifically to a biometric apparatus which carries out zero-point reset when the biometric apparatus is not in use.

2. Description of the Related Art

In the related art, various types of biometric apparatuses for measuring biometric data such as the weight, the percent body fat, the amount of body fat of a measured person are used and, a body-fat-meter-integrated weighing machine is widely used for example, at home, as one of the biometric apparatuses. Such body-fat-meter-integrated weighting machine generally includes an electrode member for measuring bioimpedance (electric resistance) of a measured person disposed on an upper surface of a body, and a weight measuring unit at a position corresponding to the electrode member. The weight measuring unit includes a load cell composed of a distortable member formed of a metallic member which is deformed according to an applied load and a strain gauge (sensor) attached to the distortable member, and the strain gauge expands or contracts according to the deformation of the distortable member due to the application of load, so that the weight of the measured person is calculated by a change of the value of resistance (output value) according to the expansion and contraction of the strain gauge as a change of a load signal output. To use such the body-fat-meter-integrated weighting machine, after having turned the power on, the measured person rides on the body, so that the biometric data such as the weight or the percent body fat is measured.

When the measured person uses the body-fat-meter-integrated weighing machine, it is necessary to place the body-fat-meter-integrated weighing machine on the floor in the room horizontally, and set the output value of the load cell in an unloaded state before the measured person rides on the body to zero point, so-called zero-point reset. It is because the weight of the measured person is measured on the basis of the difference between an output value of the load cell when the measured person rides on the weighting machine and an output value of the load cell in an unloaded state. The biometric data such as the percent body fat or the amount of body fat is obtained also by the bioimpedance measured by flowing weak constant current from the electrode members to the bottom of the measured person's feet. However, since the biometric data is computed on the basis of consideration of the weight of the measured person, adequate zero-point reset is important for obtaining accurate biometric data (JP-A-62-126318).

The body-fat-meter-integrated weighting machine in the related art as described above is generally set to put the power on first, then, after having waited until the output of the load cell is stabilized, carry out the zero-point reset. Therefore it is not convenient for the measured person because he/she cannot ride on the platform and start measurement quickly when he/she wants to measure the biometric data. Therefore there is proposed a so-called step-on type biometric apparatus which completes the zero-point reset at predetermined intervals, starts up when it detects that the measured person rides on the biometric apparatus, so that the measurement of the biometric data may be started quickly when the measured person does not use the biometric apparatus.

However, even in the case of the step-on type biometric apparatus as described above, the state of installation of the biometric apparatus when it is not in use is not necessarily in a state suitable for the zero-point setting. For example, when the biometric apparatus is stored, it may be stored in a state of being propped against a wall with one side down, or may be stored in a state in which one side of the body is in touch with the wall, which are not necessarily suitable for the zero-point reset. Therefore, when the zero-point reset of the output value of the load cell in such states which is not suitable for the zero-point reset of the biometric apparatus, the biometric data such as the weight may be calculated on the basis of the incorrect zero-point, and hence there may arise a problem in which an accurate biometric data are not measured.

Even when the biometric apparatus is installed horizontally, when an output value of the load cell is to be detected for the zero-point reset, there is a case in which the value is fluctuated due to the influence of, for example, vibrations generated around the biometric apparatus. Therefore, in order to achieve the zero-point reset accurately, it is necessary to detect the output value of the load cell for a certain period of time and reset the zero point when the output value is stabilized.

SUMMARY OF THE INVENTION

Accordingly, it is an object of the present invention to provide a biometric apparatus which is installed in a state suitable for zero-point reset, and carries out the zero-point reset when the output of a load signal is stabilized.

In order to solve the above-described problems, the invention provides a biometric apparatus which carries out zero-point reset as an output of a load signal in an unloaded state when the biometric apparatus is not in use, including a biometric unit having a predetermined zero-point for measuring a load applied to a platform provided on a body of the biometric apparatus and outputting a load signal which indicates the load; a detecting unit for detecting the state of installation of the biometric apparatus and outputting a detection signal indicating the state of installation; and a control unit connected to the biometric unit and the detecting unit for determining whether or not the state of installation is suitable for carrying out the zero-point reset for the biometric unit on the basis of the detection signal and whether or not the load signal is stabilized when the biometric apparatus is not in use, in which the zero-point reset for resetting the output of the load signal from the biometric unit to the zero-point instead of the predetermined zero-point is carried out when the control unit determines that the state of installation is suitable for carrying out the zero-point reset for the biometric unit and the load signal from the biometric unit is stable.

Preferably, the control unit carries out the determination whether or not the state of installation is suitable for the biometric unit to carry out the zero-point reset at predetermined intervals.

Preferably, the detecting unit includes an inclination sensor provided in the platform, and the control unit determines that the state of installation is suitable for carrying out the zero-point reset for the biometric unit when the platform is within a predetermined angle range with respect to the horizontal plane.

Preferably, the biometric unit includes a weight sensor for measuring the weight of a measured person.

Preferably, the control unit determines that the load signal is stable when the difference between the maximum value and the minimum value of the output of the load signal during a predetermined time does not exceed a predetermined value.

Preferably, the detecting unit includes a foot switch which sends a signal for turning the biometric apparatus on and off to the control unit, and the control unit determines upon reception of the signal from the foot switch that the state of installation is not suitable for carrying out the zero-point reset and does not carry out the zero-point reset of the biometric unit.

In this specification, the state of installation suitable for carrying out the zero-point reset means a state of installation in which the platform provided on the body of the biometric apparatus is oriented horizontally and faces upward, and no load is applied to the platform. Therefore, not only the state of installation in which the platform is inclined with respect to the horizontal plane, the upright installation, and the reverse state, but also a state in which the platform is arranged horizontally but is in contact with an obstacle are not suitable for carrying out the zero-point reset.

According to the invention, since the zero-point reset is carried out when the state of installation is suitable for carrying out the zero-point reset and when the output of the load signal is stable, the zero-point reset is carried out accurately and reliably. Therefore, the biometric data is measured further accurately.

DESCRIPTION OF THE PREFERRED EMBODIMENTS

Figure 1:
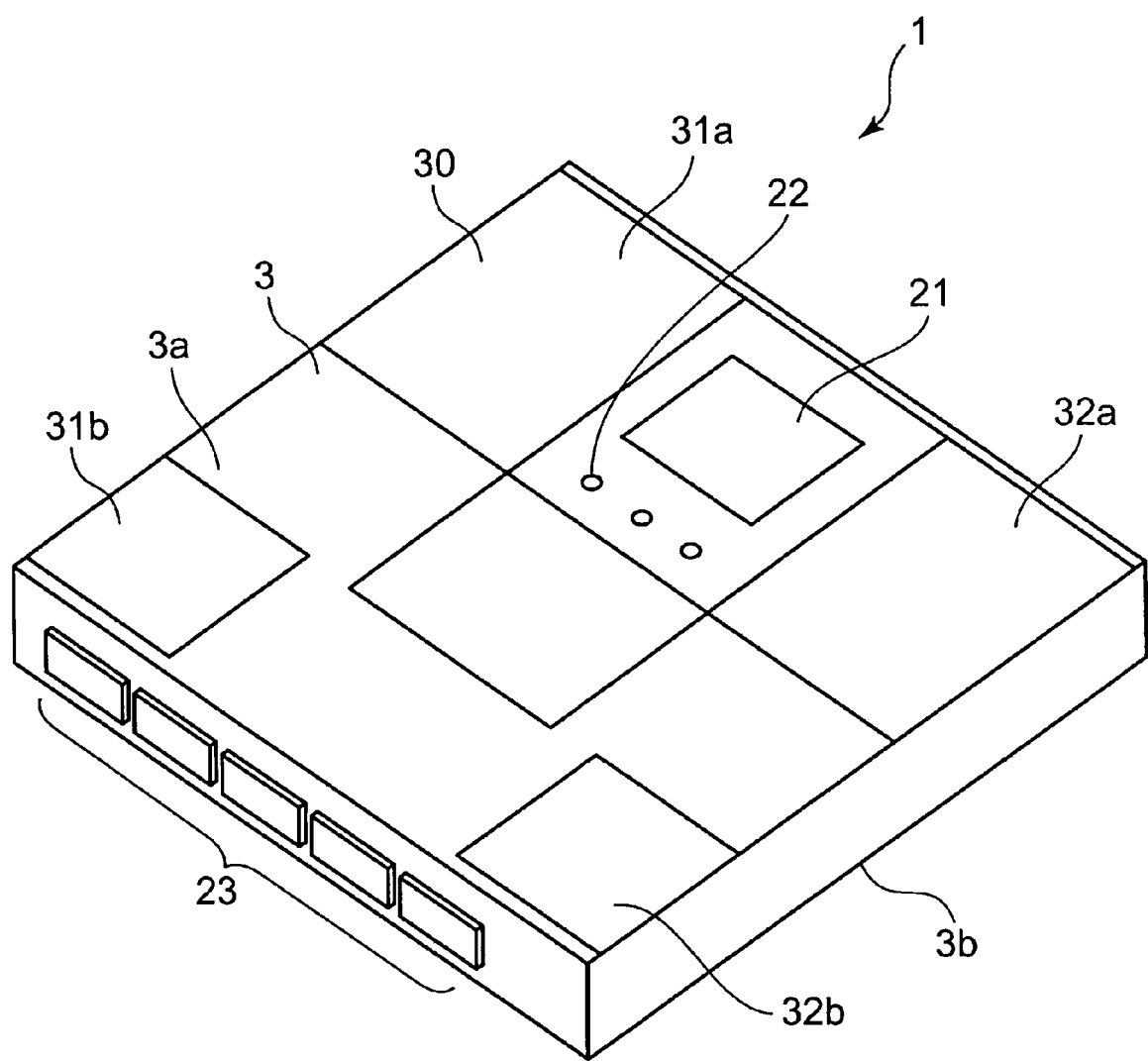
FIG. 1 is a perspective view showing a body-fat-meter-integrated weighting machine according to a first embodiment.
Figure 2:
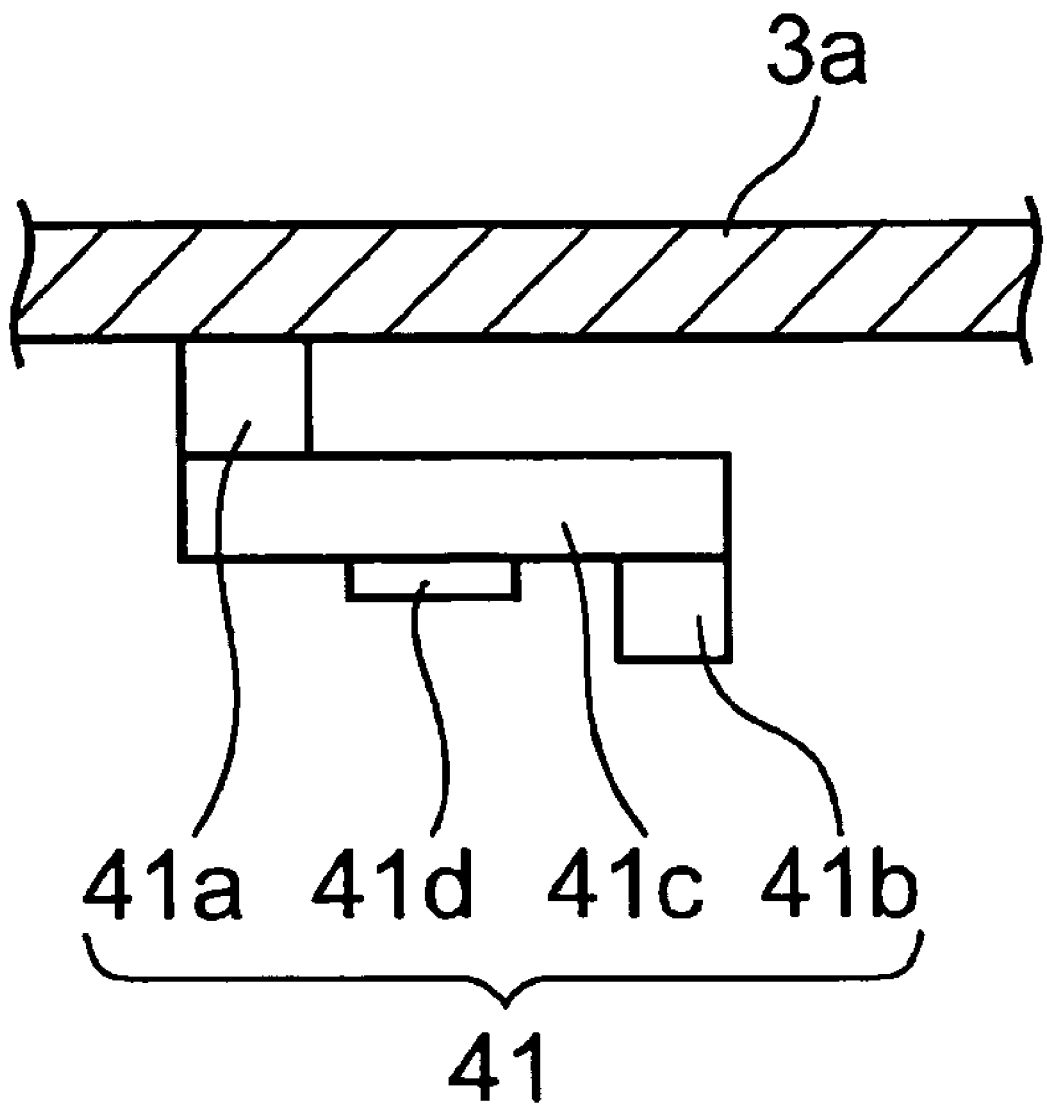
FIG. 2 is a partly cross-sectional view showing an example of a configuration of a detecting unit of the body-fat-meter-integrated weighting machine in FIG. 1.
Figure 3:
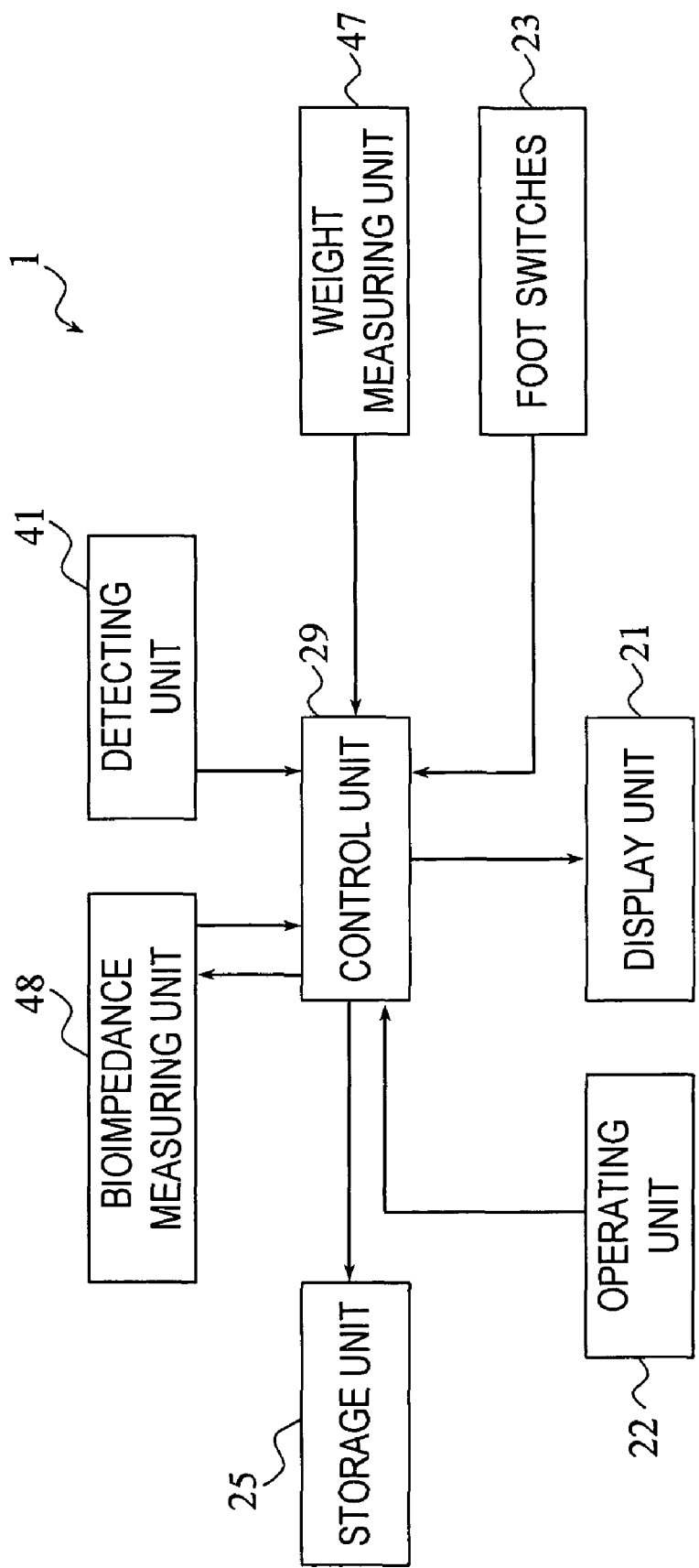
FIG. 3 is a block diagram showing the body-fat-meter-integrated weighting machine in FIG. 1.
Figure 4:
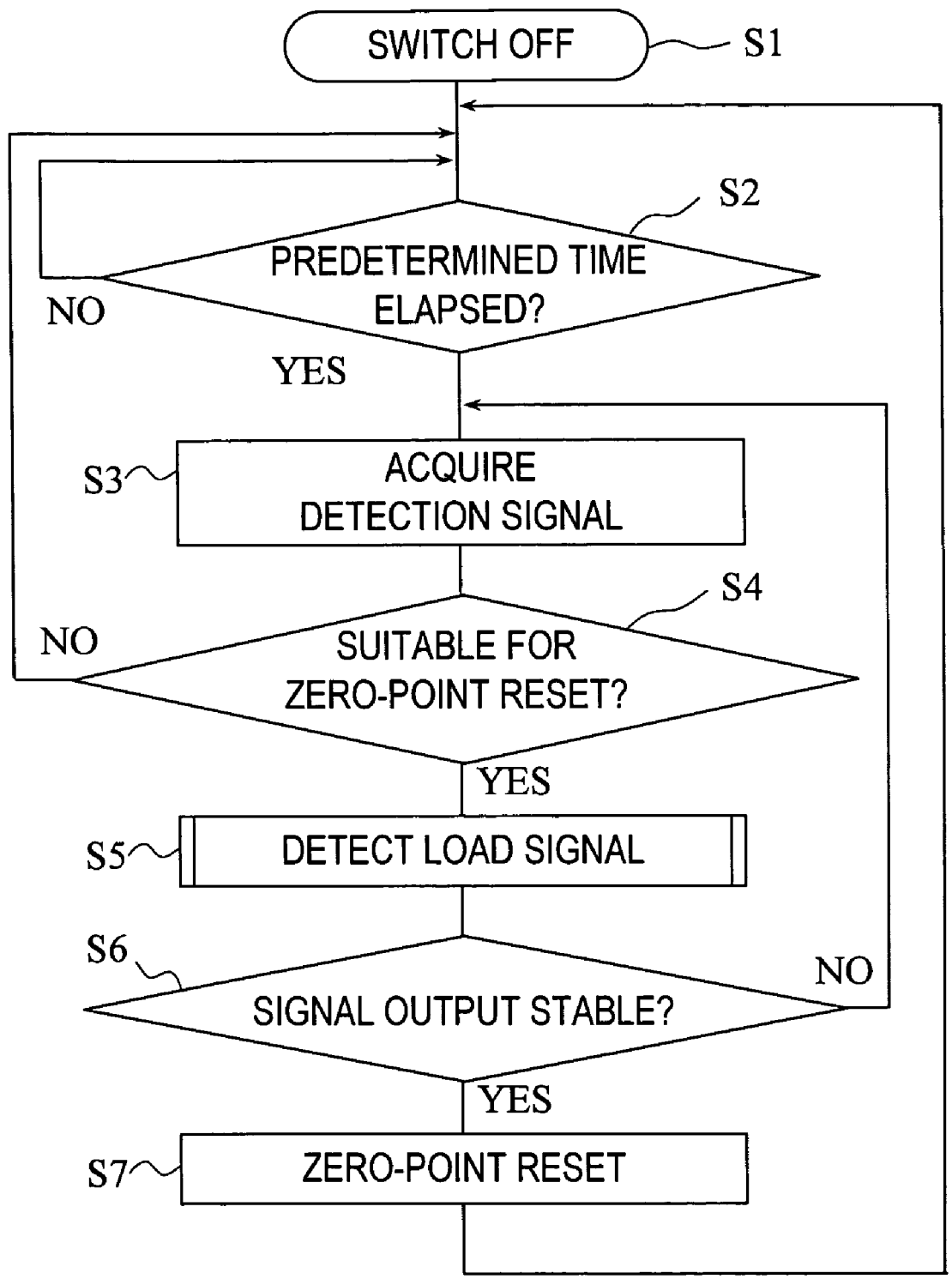
FIG. 4 is a flowchart of a zero-point reset process for the body-fat-meter-integrated weighting machine in FIG. 1.
Figure 5A:
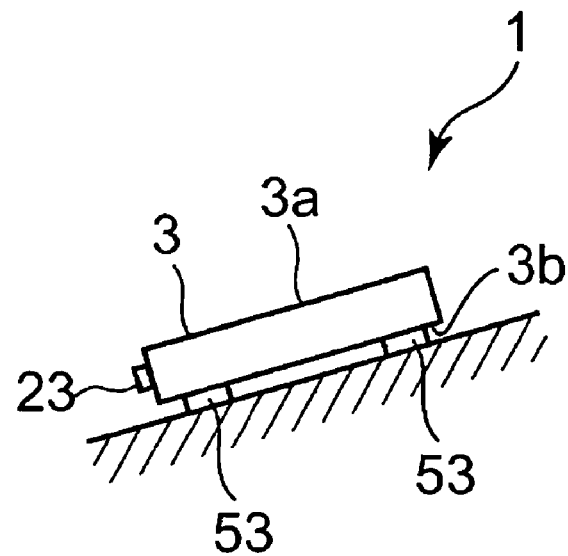
FIG. 5A is a side view showing a state in which a body-fat-meter-integrated weighting machine 1 in FIG. 1 is installed in an inclined state.
Figure 5B:
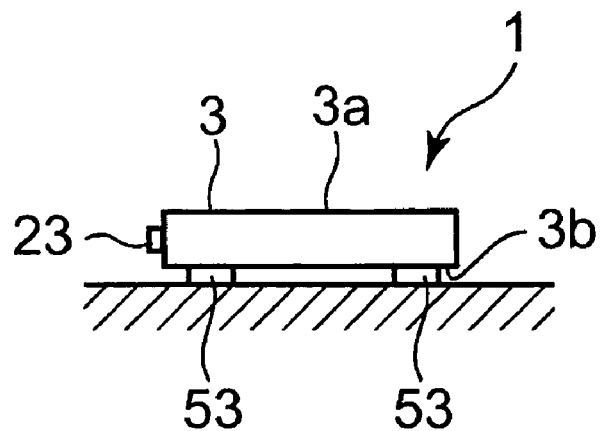
FIG. 5B is a side view showing a state in which the body-fat-meter-integrated weighting machine 1 in FIG. 1 is installed horizontally.
Figure 6:
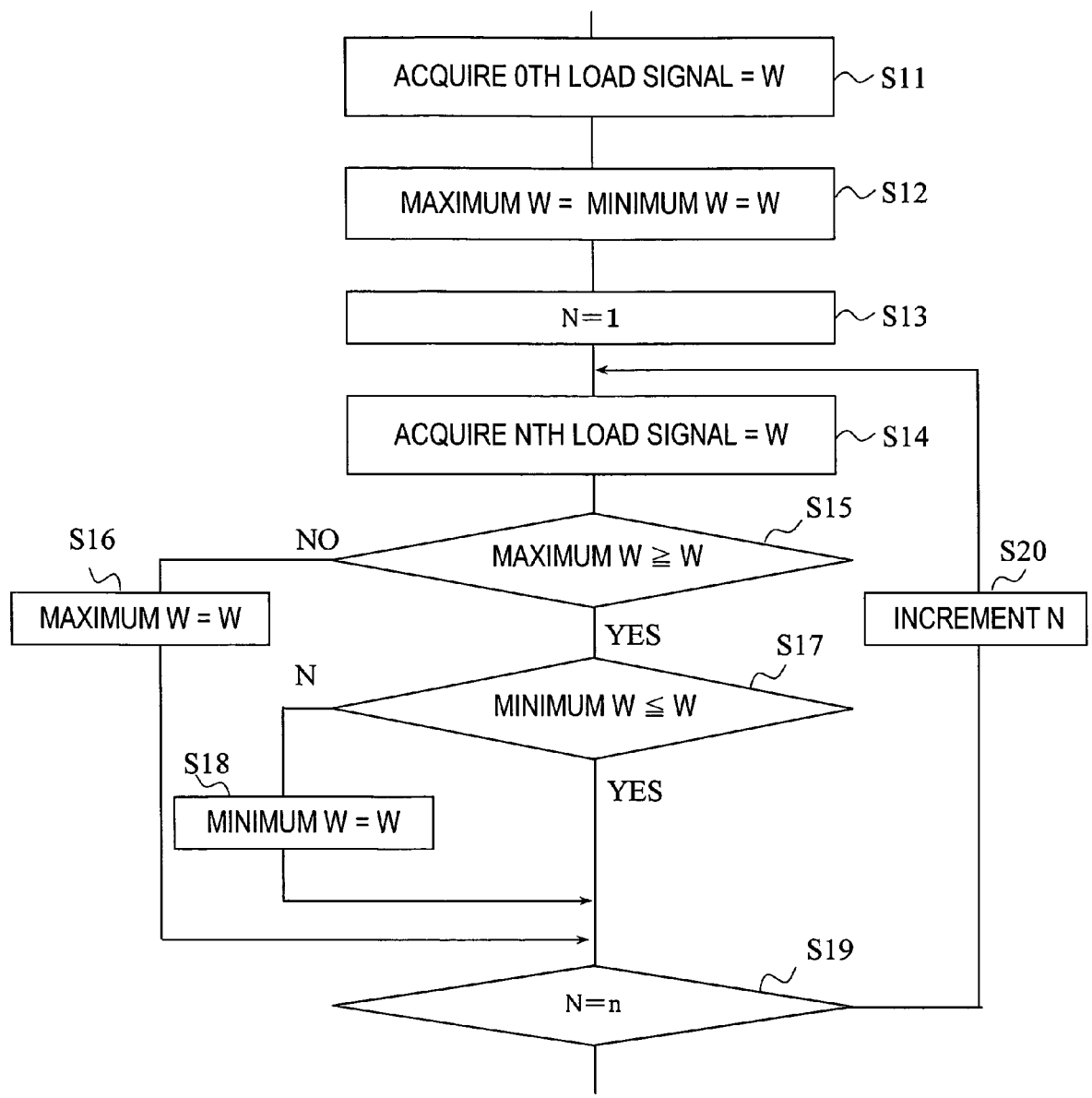
FIG. 6 is a flowchart showing detection of a signal (Step S5) in FIG. 4 in detail.

Referring now to the drawings, a first embodiment in which a biometric apparatus according to the invention is applied to a body-fat-meter-integrated weighting machine will be described. FIG. 1 is a perspective view showing a body-fat-meter-integrated weighting machine 1 according to a first embodiment; FIG. 2 is a partly cross-sectional view showing an example of a configuration of a detecting unit 41 according to the first embodiment; FIG. 3 is a block diagram showing the body-fat-meter-integrated weighting machine in FIG. 1; FIG. 4 is a flowchart of a zero-point reset process for the body-fat-meter-integrated weighting machine in FIG. 1; FIG. 5A is a side view showing a state in which the body-fat-meter-integrated weighting machine 1 in FIG. 1 is installed in an inclined state; FIG. 5B is a side view showing a state in which the body-fat-meter-integrated weighting machine 1 in FIG. 1 is installed horizontally; and FIG. 6 is a flowchart showing detection of a load signal (Step S5) in FIG. 4 in detail. A control unit 29, a storage unit 25, the detecting unit 41, and a weight measuring unit 47 arranged in the interior of a body 3, being shown in FIG. 3, are omitted in FIG. 1 since they are internal mechanisms.

As shown in FIG. 1, FIG. 2 and FIG. 5A, the body-fat-meter-integrated weighting machine 1 (hereinafter, referred to as weighting machine 1) according to the first embodiment includes the body 3 formed into a substantially box shape, and legs 53 provided on a back surface 3b of the body 3 for supporting the body 3. The body 3 includes a platform 3a, a bioimpedance measuring unit 48 having electrode members 30 (conducting electrodes 31a, 32a, measuring electrodes 31b, 32b), the weight measuring unit 47 as the weight measuring unit, a display unit 21, an operating unit 22, foot switches 23, the storage unit 25, the control unit 29, a power source for supplying an electric power (not shown), and the detecting unit 41 for detecting a state of installation of the weighting machine 1 and outputs a detection signal showing the state of installation. Detailed configurations of the members are described in detail.

The body 3 is formed into a substantially box shape by combining rectangular plate-shaped members (covering member and the bottom plate member) formed by molding a resin (for example, ABS resin (acrylonitrile/butadiene/styrene copolymer)) or the like, and includes the platform 3a on which a measured person rides on the upper surface of the body 3. Considering the strength of the weighting machine 1 as a product, the body 3 may be formed in combination of the rectangular plate-shaped member (cover member) in the resin on the side of the platform 3a and the rectangular plate-shaped member in metal on the opposite side (bottom plate member).

As shown in FIG. 1, the thin plate-shaped four electrode members 30 (conducting electrodes 31a, 32a, measuring electrodes 31b, 32b) are held on the platform 3a of the body 3, and are arranged apart from each other on the surface of the platform 3a. Although the structure for holding the electrode members 30 may be selected as needed, for example, it is suitable to form recesses (not shown) for fitting the electrode members 30 on the platform 3a of the body 3, and hold the same in a state of being fitted so that the electrode members 30 and the platform 3a are flush with each other (see FIG. 1). The electrode members 30 correspond the bioimpedance measuring unit 48 as described later.

As shown in FIG. 1, the platform 3a of the body 3 is provided with the display unit 21 and the operating unit 22 in addition to the electrode members 30. On the side surface of the body, a foot switch 23 including a plurality of switches is arranged. The display unit 21 is mainly for displaying the biometric data and, for example, a liquid crystal display such as a full dot LCD is employed. The operating unit 22 may be, for example, of button type, touch sensor type or dial type.

A known inclination sensor may be used as the detecting unit 41 and, as shown in FIG. 2 for example, a configuration including a fixed member 41a fixed to the lower surface (back surface) of the platform 3a, a distortable member 41c which is fixed at one end to the fixed member 41a in a cantilevered manner and has a weight 41a at the other end, and a distortion detecting element 41d attached to the distortable member 41c, so as to measure the amount of distortion of the distortable member 41c when the fixed member 41a is inclined with the platform 3a by the distortion detecting element 41d is applicable. Whether or not the body 3 is horizontal is determined by the control unit 29 on the basis of the amount of distortion measured by the distortion detecting element 41d.

As shown in FIG. 3, the display unit 21, the operating unit 22, the foot switches 23, the detecting unit 41, the weight measuring unit 47 and the bioimpedance measuring unit 48 are connected to the control unit 29, and are controlled thereby. The control unit 29 is also connected to the power source (not shown) and the storage unit (for example, RAM (Random Access Memory)) 25. A battery or an external power source for supplying an electric power for activating the weighting machine 1 may be used as the power source.

The weight measuring unit 47 as the weight measuring unit may be a load cell including a distortable member formed of a metallic member which is deformed according to a load applied thereto and a strain gauge to be mounted to the distortable member, so that the distortable member is fixed at a fixed end thereof to the body 3, whereby the a movable end of the distortable member is supported by the legs 53. Accordingly, when the measured person rides on the platform 3a of the body 3 and the distortable member is distorted by the load, the strain gauge expands and contracts, and the value of resistance (output value) according to the expansion and contraction of the strain gauge is changed, so that the weight is measured by the change of resistance as the change of the load signal output. The control unit 29 obtains the weight by calculating the difference between the value of resistance (output value) from the weight measuring unit 47 when no load is applied to the body 3 and the value of resistance (output value) when the load is applied thereto, so that the weight of the measured person is measured.

The bioimpedance measuring unit 48 includes the electrode members 30 having the conducting electrodes 31a, 32a, and the measuring electrodes 31b, 32b which are adapted to come into contact with the feet of the measured person, a constant current feeding unit (not shown) connected to the conducting electrodes 31a, 32a for providing a high-frequency weak constant current and a voltage measuring unit (not shown) connected to the measuring electrodes 31b, 32b for measuring the potential difference of the living body. In this embodiment, the pair of conducting electrode 31a and the measuring electrode 31b are arranged so as to come into contact with the bottom of the left foot, and the pair of conducting electrode 32a and the measuring electrode 32b are arranged so as to come into contact with the bottom of the right foot. A weak constant current is provided from the constant current feeding unit through the conducting electrodes 31a, 32a for the left foot and the right foot, respectively, from the toes to the legs (lower half body) of the measured person, the potential difference at the measuring electrodes 31b, 32b (heel portions) of this current path is measured by the voltage measuring unit, so that the measurement of the bioimpedance is carried out.

The operating unit 22 is input means for entering personal information such as height, sex and age, and setting items for each person. The entered biometric data and setting items for each person is stored in the storage unit 25 (for example, RAM) or displayed on the display unit 21.

The foot switches 23 are connected to the control unit 29 and are adapted to turn the weighting machine 1 on and off by sending a signal to the control unit 29 and, are capable of calling up the personal information or the setting items when they stored in the storage unit 25 in advance. For example, when a plurality of the measured persons use the weighting machine 1, each of the plurality of foot switches 23 is assigned to each measured person, whereby the measured person is able to call up his/her own personal information or the setting items by pressing the assigned foot switch 23. The setting items here are the setting items necessary for the measured person (user) when using the weighting machine 1, such as the size of characters or signs of the biometric data and the type of the biometric data to be displayed on the display unit 21.

A control system of the weighting machine 1 will be described. As shown in FIG. 3, the control unit 29 is electrically connected to the detecting unit 41, the display unit 21, the operating unit 22, the foot switches 23, the storage unit 25, the weight measuring unit 47 and the bioimpedance measuring unit 48.

When the weighting machine 1 is not in use, that is, when the power source of the weighting machine 1 is turned off, the control unit 29 receives a detection signal from the detecting unit 41. On the basis of the signal, the control unit 29 determines whether or not the zero-point reset of the weight measuring unit 47 is to be carried out. The weight measuring unit 47 then sends an output value relating to the load applied to the platform 3a to the control unit 29. The control unit 29 determines whether or not the output of the load signal from the weight measuring unit 47 is stable, or calculates the weight on the basis of the load signal. The obtained weight is displayed on the display unit 21 or stored in the storage unit 25.

The control unit 29 calculates the bioimpedance on the basis of the potential difference acquired by the bioimpedance measuring unit 48 and the provided constant current, and calculates the percent body fat or the amount of body fat. The percent body fat obtained by calculation is displayed on the display unit, or stored in the storage unit 25.

Referring now to FIG. 4, the process of the zero-point reset of the weighting machine 1 will be described below. The weighting machine 1 is in a state of not being used for measuring the biometric data, that is, in a state in which the power source is turned off (Step S1). Then, determination of whether or not a predetermined time is elapsed since the weighting machine 1 is turned off is carried out by a clock circuit of the control unit 29 (Step S2). When the predetermined time has elapsed, the control unit 29 acquires a detection signal indicating the angle of inclination of the platform 3a from the inclination sensor which corresponds to the detecting unit 41 (Step S3). The control unit 29 determines whether or not the weighting machine 1 is in a state of installation suitable for carrying out the zero-point reset of the weight measuring unit 47 on the basis of the detection signal (Step S4).

More specifically, when the angle of inclination of the platform 3a with respect to the horizontal plane exceeds a predetermined range, it is determined that the state of installation is not suitable for carrying out the zero-point reset of the weight measuring unit 47 (see FIG. 5A). In this case, the procedure goes back to Step S2 and the zero-point reset is not carried out. Then, after having elapsed the predetermined time, the detection signal is acquired again (Step S3), and whether or not the state of installation is suitable is determined (Step S4). In contrast, when the angle of inclination of the platform 3a is within the predetermined range (see FIG. 5B), and the state of installation is determined to be suitable for carrying out the zero-point reset of the weight measuring unit 47, a load signal (value of resistance) from the load cell of the weight measuring unit 47 is detected (Step S5).

The load signal detected by the weight measuring unit 47 is sent to the control unit 29, and the control unit 29 determines whether or not the output of the signal is stable (Step S6). Determination of whether or not the output of the load signal is stable is carried out by whether or not the difference between the maximum value and the minimum value of the output of the load signal does not exceed a predetermined value. When the difference between the maximum value and the minimum value of the output of the load signal from the load cell of the weight measuring unit 47 does not exceed the predetermined value, the control unit 29 carries out the zero-point reset to replace the zero-point of the weight measuring unit 47 with a newly measured load signal output (Step S7). The zero-point to be reset may be set as desired such as a mean value of the output of the load signal obtained in Step S5 or a value obtained by adding the maximum value and the minimum value and dividing the sum by two.

In contrast, when the difference between the maximum value and the minimum value of the output of the load signal from the load cell of the weight measuring unit 47 exceeds the predetermined value (for example, when vibrations occur around the weighting machine 1), the control unit 29 determines that the load signal is not stable, and hence the zero-point reset is not carried out (that is, the zero-point which is already set is maintained), and the procedure goes back to Step S3, where the process of determining whether or not the state of installation is suitable for carrying out the zero-point reset in Step S4 (Step S4 to Step S6) is repeated as described above.

Referring now to FIG. 6, the signal acquiring process (Step 5) which is carried out for determining the stability of the output of the load signal from the load cell of the weight measuring unit 47 will be described in detail. The control unit 29 receives the load signal from the load cell of the weight measuring unit 47 for a predetermined time (for example, t seconds) from the beginning of measurement. The load signal from the weight measuring unit 47 is converted into a digital signal by an A/D conversion circuit in the control unit 29. The number of output data after having digitized (for example, n+1 (0–n) for the predetermined time length t) may be set as needed.

The $0^{th}$ output of the load signal is assumed to be W (Step S11). Then, the maximum value (maximum W) of the output and the minimum value (minimum W) of the output are assumed to be W (Step S12). Then, a variable N for carrying out the load signal acquiring process is set to be 1 (Step S13).

Then, the output of the first load signal is assumed to be W (Step S14). The output W is compared with the maximum W set in Step S12 described above (Step S15). When the maximum W is smaller than the output W, the W is reset to be the maximum W (Step S16). On the contrary, when the maximum W is at least equal to the output W, the procedure goes to Step S17. In Step S17, determination of whether or not the minimum W set in Step S12 is equal to or smaller than the output W is carried out. When the minimum W is equal to or smaller than the output W, the procedure goes to Step S19 and when the output W is smaller than the minimum W, the output W is reset as the minimum W (Step S18).

Then, whether or not the variable N is equal to the number of repetition n is determined (Step S19). When N is equal to the output number of data n, the process in Step S16 is ended, and determination of whether or not the load signal output is stable is carried out in Step S6. The processes from Step S17 to Step S20 are repeated such that N is incremented in Step S20 when the variable N is not equal to n, and the next load signal output W is acquired in Step S14.

As described above, in this embodiment, the weighting machine 1 is controlled in such a manner that the zero-point reset is carried out when it is determined that the state of installation is suitable for the weighting machine 1 to carry out the zero-point reset and that the load signal from the load cell of the weight measuring unit 47 is stable. Since the accurate zero-point reset of the weighting machine 1 is accomplished by reflecting the newest information about the environment or conditions where the weighting machine 1 is installed when using the weighting machine 1, the biometric data is measured with high degree of accuracy, so that a user friendly weighting machine is realized. In particular, in the case of the so-called step-on weighting machine which is activated when the fact that the measured person rides on the weighting machine is detected, and then starts measurement of the biometric data, the zero-point reset needs to be carried out when the weighting machine is not in use. Therefore, when the invention is applied, the weighting machine may go standby always in a state in which the accurate zero-point reset is completed, so that accurate measurement of the weight and other biometric data is achieved.

A method of carrying out the biometric measurement by the measured person using the weighting machine 1 will be described in brief. The measured person presses the foot switch 23 and brings the weighting machine 1 to be ready to measure the biometric data. Then, when the measured person rides on the body 3, the biometric data such as weight, percent body fat, amount of body fat, offal fat, or body age of the measured person is calculated using the already reset zero-point, and the biometric data is displayed on the display unit 21. When the weighting machine 1 is configured as the step-on weighting machine, the weighting machine 1 may be adapted to detect the fact that the measured person rides on the body without being pressed the foot switch by the measured person and to be activated to start measurement of the weight and, when measuring the weight, to use the zero-point which is already reset.

This embodiment is configured to determine whether or not the body 3 is inclined by using the inclination sensor as the detecting unit 41. However, the invention is not limited to this configuration. For example, the foot switches 23 may be used as the detecting unit 41. It is because in a state of installation in which the foot switches 23 are pressed by the obstacle such as the wall even when the body 3 is installed horizontally with the upper surface faced upward, the bioimpedance measuring unit 48 may be applied with some load, and if the weight is measured from the zero-point in this state, the weight may not be measured accurately. In this case, a configuration in which the control unit 29 determines that the state of installation is not suitable for carrying out the zero-point reset of the weight measuring unit 47 when the foot switches 23 are pressed downward and hence the control unit 29 receives the signal indicating on and off is also applicable without providing an inclination sensor (of course, it may also be used together). In this manner, it is needless to say that any means may be employed as needed as the detecting unit as long as it is able to determine the state of installation, such that the body 3 is horizontal, the platform faces upward, and no load is applied to the platform.

Furthermore, when the plurality of foot switches 23 are provided as in this embodiment, a configuration in which when at least two foot switches 23 are pressed simultaneously and the control unit 29 which receives the signal determines that the state of installation of the weighting machine 1 is not suitable for the zero-point reset, and does not carry out the zero-point reset is also applicable.

In the embodiment shown above, when it is determined that the load signal is not stable (Step S7), the detection signal is acquired (Step S3) after having elapsed the predetermined time (Step S2). However, a configuration in which the Steps S3 and S4 for detecting the state of installation are omitted and the load signal is to be acquired again after having elapsed the predetermined time (Step S5) is also applicable.

Although the embodiment shown above is configured to acquire the plurality of biometric data, it is needless to say that the invention is applicable also to the weighting machine for measuring only the weight of the measured person as a single biometric data.

The invention is embodied in other various modes without departing from the scope of the invention. Therefore, the embodiment shown above is illustrative only, and is not intended to limit the invention, as a matter of course.

What is claimed is:

1. A biometric apparatus which carries out zero-point reset as an output of a load signal in an unloaded state when the biometric apparatus is not in use, the biometric apparatus comprising:

a weight measuring unit having a predetermined zero-point for measuring a load applied to a body of the biometric apparatus and outputting a load signal which indicates the load;

an inclination sensor for measuring an inclination angle of the biometric apparatus with respect to the horizontal plane and outputting a signal indicative of the measured inclination angle; and a control unit connected to the weight measuring unit and the inclination sensor for determining whether or not the measured inclination angle is within a predetermined angle range with respect to the horizontal plane on the basis of the signal at predetermined intervals and whether or not the load signal is stabilized when the biometric apparatus is not in use, wherein the zero-point reset for resetting the output of the load signal from the weight measuring unit to the zero-point instead of the predetermined zero-point is carried out by the control unit when the control unit determines that the measured inclination angle is within a predetermined angle range with respect to the horizontal plane and the load signal from the weight measuring unit is stable, and the zero-point reset is not carried out by the control unit when the control unit determines that the measured inclination angle is not within the predetermined angle range with respect to the horizontal plane.

2. The biometric apparatus according to claim 1, wherein the control unit carries out the determination whether or not the state of installation is suitable for the weight measuring unit to carry out the zero-point reset at predetermined intervals.

3. The biometric apparatus according to claim 1, wherein the control unit determines that the state of installation is suitable for carrying out the zero-point reset for the weight measuring unit when the measured inclination angle is within a predetermined angle range with respect to the horizontal plane.

4. The biometric apparatus according to claim 1, wherein the weight measuring unit includes a weight sensor for measuring the weight of a measured person.

5. The biometric apparatus according to claim 1, wherein the control unit determines that the load signal is stable when the difference between the maximum value and the minimum value of the output of the load signal during a predetermined time does not exceed a predetermined value.

6. The biometric apparatus according to claim 1, wherein the biometric apparatus further includes a foot switch which sends a signal for turning the biometric apparatus on and off to the control unit, and the control unit determines upon reception of the signal from the foot switch that the state of installation is not suitable for carrying out the zero-point reset and does not carry out the zero-point reset of the weight measuring unit.

* * * * *